US00PP29261P3

(12) United States Plant Patent
Olesen

(10) Patent No.: US PP29,261 P3
(45) Date of Patent: May 1, 2018

(54) MINIATURE ROSE PLANT NAMED 'POULPAH081'

(50) Latin Name: ***Rosa* hybrid**
Varietal Denomination: Poulpah081

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days. days.

(21) Appl. No.: 15/330,293

(22) Filed: Sep. 6, 2016

(65) Prior Publication Data

US 2018/0070501 P1 Mar. 8, 2018

(51) Int. Cl.
*A01H 5/02* (2006.01)

(52) U.S. Cl.
USPC ..... Plt./120

(58) Field of Classification Search
USPC ..... Plt./120, 118, 119, 121
CPC ..... A01H 5/0222
See application file for complete search history.

(56) References Cited

PUBLICATIONS http://www.poulsenroser.com/assortment/rose-collections/patiohit/lafayette-2015-hit.aspx; No date; 1 page.*
https://www.zauba.com/import-cut-rose/hs-code-06024000-hs-code.html; No date; 0 pages.*

* cited by examiner

*Primary Examiner* — Kent L Bell

(57) ABSTRACT

A new garden rose plant of the Miniature class which has abundant, yellow-apricot blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulpah081'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah081', originated as a single seedling from the stated cross.

The new variety may be distinguished from its male pollen parent and female seed parent primarily by the following characteristics. The male pollen parent plant has white flowers while the new variety has yellow-apricot blend colored flowers. The female seed parent plant has orange flowers, while the new variety has yellow-apricot blend flowers.

The objective of the hybridization of this rose variety was to create a new and distinct variety for garden use with unique qualities, such as:

1. Uniform and abundant yellow-apricot blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah081' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah081' was selected in the spring of 2011 by the inventor as a single plant from the progeny of the aforementioned hybridization.

Asexual reproduction of 'Poulpah081' by traditional budding and rooted cuttings was first done by Mogens N. Olesen in the nursery in Fredensborg, Denmark in July, 2011. This initial and other subsequent asexual propagations conducted in controlled environments have demonstrated that the characteristics of 'Poulpah081' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah081'.

Specifically illustrated in FIG. 1 of the drawing is an open flower viewed from above, flowers at various stages of opening viewed from the side, flower petals detached, sepals detached, and reproductive flower parts.

DETAILED DESCRIPTION OF THE VARIETY

Figure 1:
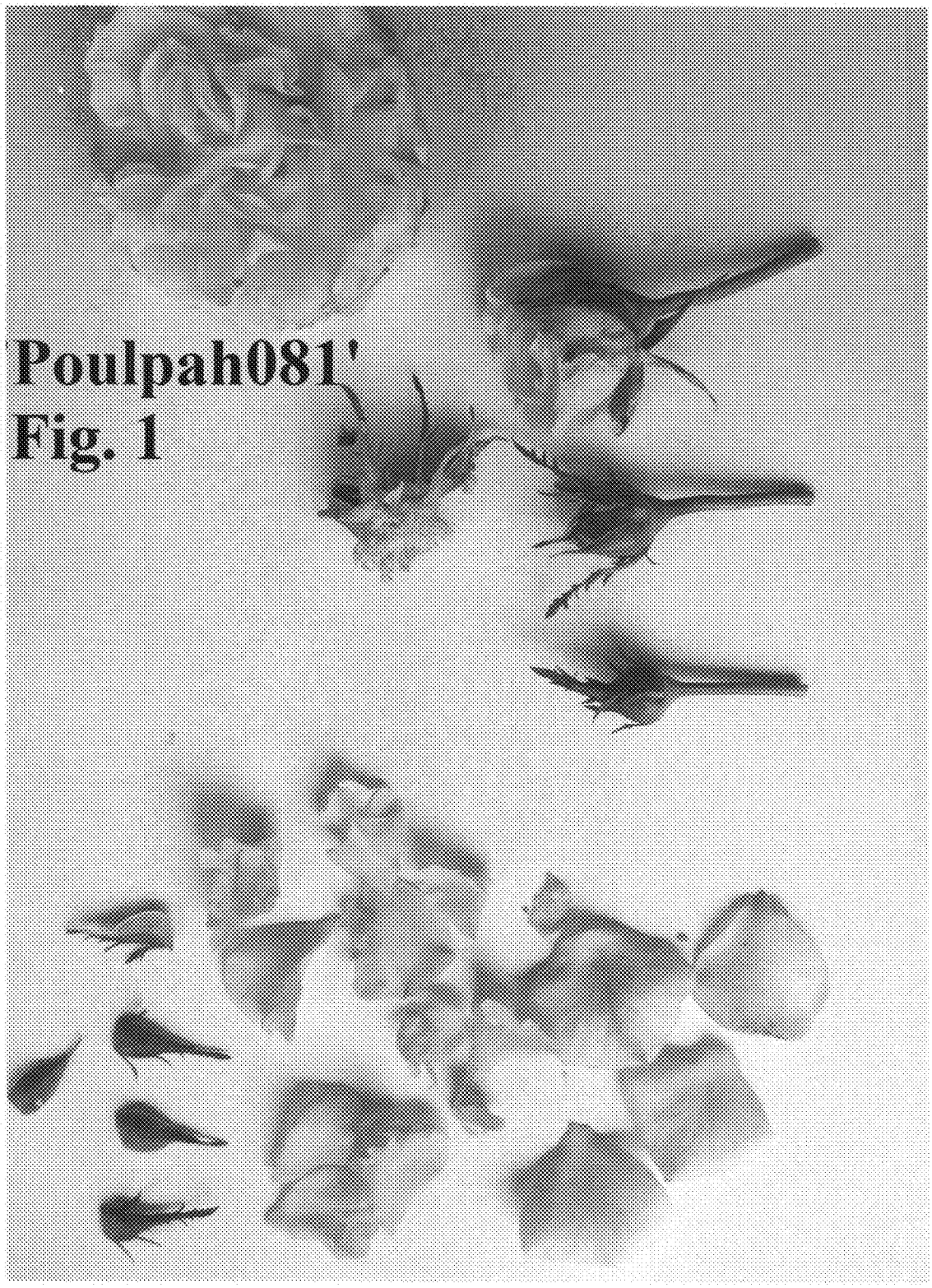
Figure 2:
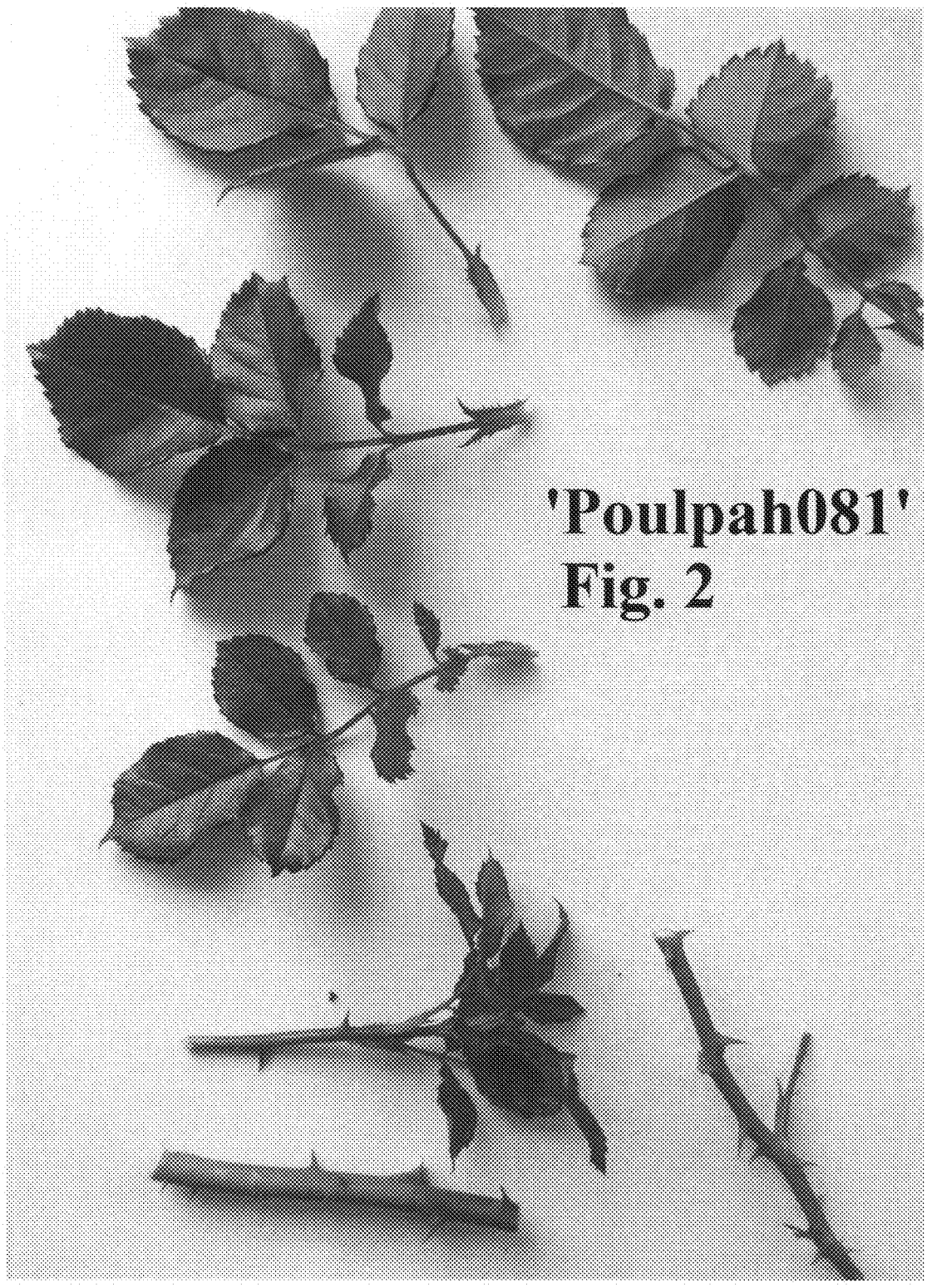
FIG. 2 shows mature and juvenile leaves, mature and juvenile bare stems.
Figure 3:
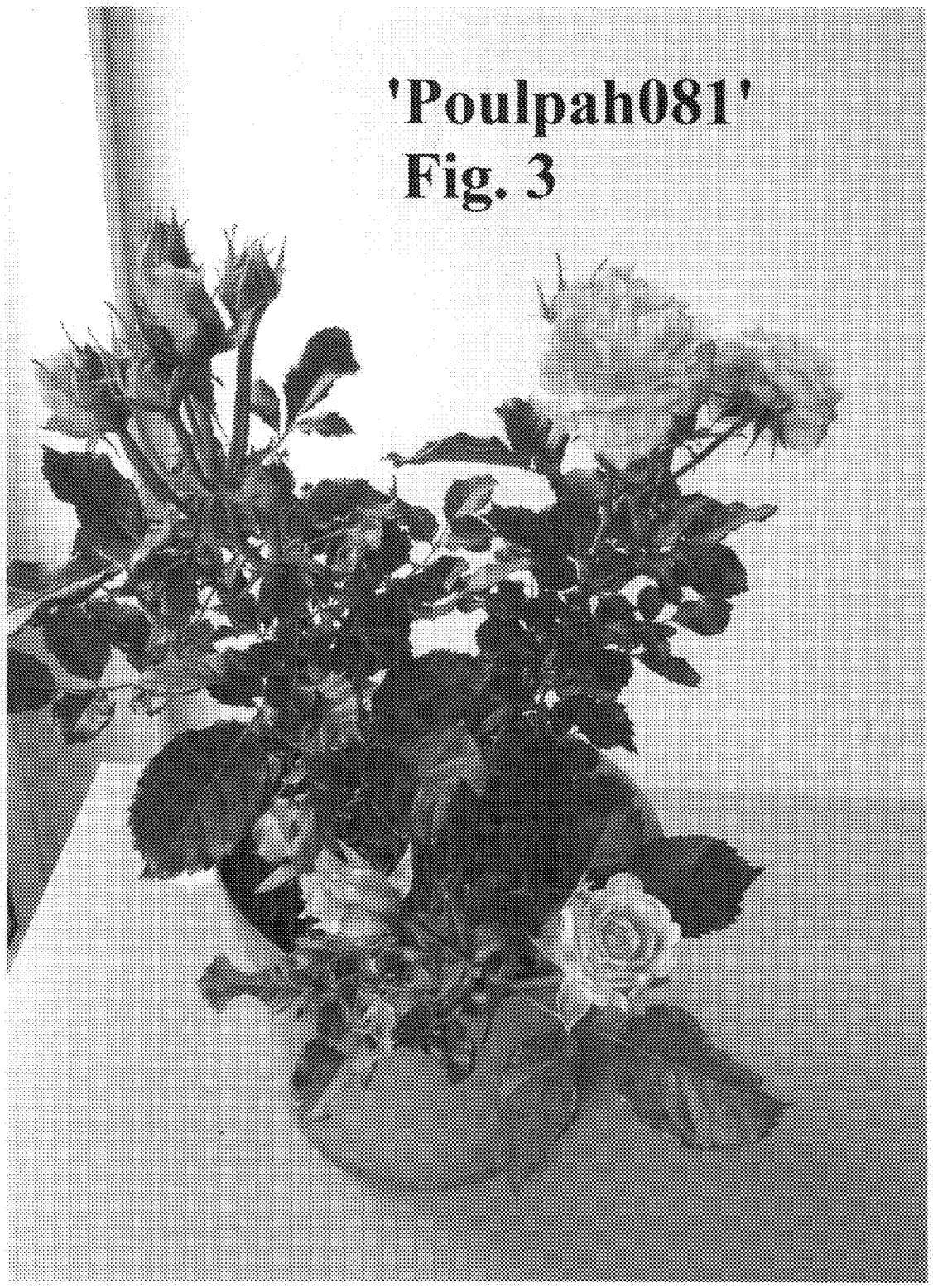
FIG. 3 shows the whole plant flowering in a 21 cm container. Plants shown are 1 year old.

The following is a description of 'Poulpah081', as observed in its growth at a container nursery in Odense Denmark. Observed plants are 1 year old, and were grown on their own roots in 21 cm containers. Color references are made using The Royal Horticultural Society (London, England) Colour Chart, 2001, except where common terms of color are used.

For a comparison, several physical characteristics of the rose variety 'Poulsiv', U.S. Plant Pat. No. 13,104 are compared to 'Poulpah081' in Chart 1.

CHART 1

| | 'Poulpah081' | 'Poulsiv' |
|---|---|---|
| Petal Count | 60 | 50 to 55 |
| Flower Diameter | 60 to 70 mm | 40 mm |
| General Tonality of Flower Color | Yellow-Orange Group 20C | Yellow Group 8 A-B |

FLOWER AND FLOWER BUD

Blooming habit: Continuous.

Flower bud:

*Size*.—Upon opening, 30 mm in length from base of receptacle to end of bud. Bud diameter is 13 mm.

*Bud form*.—Urceolate.

*Bud color*.—As sepals divide petals are Red Group 42B.

*Sepal inner surface*.—Color: Yellow-Green Group 148C. Surface: Lightly pubescent.

*Sepal outer surface*.—Color: Yellow-Green Group 144A with intonations of Greyed-Purple Group 184A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—20 to 27 mm long, 8 mm wide.

*Receptacle*.—Texture: Smooth. Size: 4 mm in height, 6 mm wide. Color: Yellow-Green Group 146C with intonations of Greyed-Purple Group 184A. Shape: Funnel.

*Pedicel*.—Surface: Smooth. Length: About 45 mm. Diameter: 3.5 mm on average. Color: Yellow-Green Group 144B. Strength: Strong.

*Peduncle*.—Length: 3 to 12 cm. Diameter: About 4 mm. Color: Yellow-Green Group 144A. Texture: Smooth.

Flower bud development: Flower buds are borne in corymbs up to 5 flower buds per stem.

Flower bloom:

*Fragrance*.—None.

*Duration*.—The blooms have a duration on the plant of approximately 15 days. Petal drop not easy.

*Size*.—Flower diameter is 60 to 70 mm when open. Flower depth is 25 mm.

*Flower shape*.—Rosette Very double flower with many slightly overlapping petals of different sizes.

*Shape of flower, side view*.—The upper portion is flat. The lower portion is concave.

Petalage: Under normal conditions, flowers have about 60 petals.

General tonality of flower: Open flowers are Yellow-Orange Group 20C.

Petal color:

*Upon opening, outer petals*.—Upper surface: Yellow-Orange Group 23C tipped with intonations of Red Group 39C. Lower surface: Yellow-Orange Group 22C tipped with intonations of Red Group 39C.

*Upon opening, inner petals*.—Upper surface: Orange Group 25B. Lower surface: Orange Group 24D.

*Basal petal spots, upon opening*.—No distinctive coloration at the petal base observed.

*After opening, outer petals*.—Upper surface: Yellow-Orange Group 20D. Lower surface: Yellow-Orange Group 19B.

*After opening, inner petals*.—Upper surface: Yellow-Orange Group 20B. Lower surface: Yellow-Orange Group 19B.

*Basal petal spots, after opening*.—No distinctive coloration at the petal base observed.

Petals:

*Petal reflex*.—Somewhat reflexed.

*Margin*.—Entire and uniform. Moderate to weak undulations. Occasionally a cleft in the margin.

*Shape*.—Broad elliptic. Apex shape: Rounded and emarginate. Base shape: Rounded.

*Size*.—30 mm (l)×30 mm (w).

*Texture*.—Smooth.

*Thickness*.—Average.

Petaloids:

*Size*.—15 mm (l) by 10 mm (w).

*Quantity*.—About 10.

*Shape*.—Irregular, asymmetric, with an acute base and apex.

*Color*.—Upper surface is Yellow-Orange Group 20B. Lower surface is Yellow-Orange Group 19B.

Reproductive flower parts:

*Pollen*.—None observed.

*Anthers*.—Size: 2 mm in length. Color: Yellow-Orange Group 22A. Quantity: 100 on average.

*Filaments*.—Color: Yellow-Orange Group 22A. Length: 4 to 6 mm.

*Pistils*.—Length: 4 to 6 mm. Quantity: 90 on average.

*Stigmas*.—Color: Yellow Group 2C.

*Styles*.—Color: Yellow Group 1D.

*Location of stigmas*.—Level in location relative to the length of the filaments and the height of the anthers.

*Hips*.—None Observed.

PLANT

Plant growth: Upright, bushy. Plants are 35 cm in height, and 35 cm wide.

Stems:

*Color*.—Juvenile growth: Yellow-Green Group 144B with intonations of Greyed-Purple Group 183B. Mature growth: Yellow-Green Group 144A.

*Length*.—On average, canes are 30 cm from the base of the plant to the flowering portion.

*Diameter*.—5 to 6 mm.

*Internodes*.—On mature canes about 20 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 7 mm.

*Shape*.—Upper portion is convex. Lower portion is deep concave.

*Color*.—Juvenile prickles: Greyed-Purple Group 186A. Mature prickles: Greyed-Purple Group 186B.

Plant foliage:

*Compound leaf*.—100 to 120 mm (l)×60 to 80 (w).

*Quantity*.—About 4 leaves per 10 cm of stem on average.

*Leaf bearing angle to the stem*.—45 degrees.

*Color of juvenile foliage*.—Upper side: Greyed-Purple Group 183A. Lower side: Greyed-Purple Group 182C.

*Color of mature foliage*.—Upper side: Yellow-Green Group 147A. Lower side: Yellow-Green Group 148B.

Plant leaves and leaflets:

*Stipules*.—Size: 12 mm long, mm wide. Quantity: 2 per compound leaf. Shape: Linear, slightly broad based with outward extending apices. Margins: Finely serrated. Color: Yellow-Green Group 147A.

*Petiole*.—Length: About 20 mm. Diameter: 2 mm.

*Upper surface*.—Color: Yellow-Green Group 146A.

*Lower surface*.—Color: Yellow-Green Group 146B.

*Rachis*.—Length: About 20 mm. Diameter: About 2 mm.

*Upper surface*.—Color: Yellow-Green Group 146A.

*Lower surface*.—Color: Yellow-Green Group 146B.

*Leaflet*.—Quantity: Normally 5 to 7 leaflets. Margins: Serrated. Size: On average terminal leaflets are 55 mm long, 32 mm wide. Shape: Generally ovate. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah081', substantially as illustrated and described herein, due to its abundant yellow-apricot blend flowers, disease resistance, and extended period of bloom.

* * * * *

'Poulpah081'

'Poulpah081'

'Poulpah081'